US009173659B2

(12) United States Patent
Bodewadt et al.

(10) Patent No.: US 9,173,659 B2
(45) Date of Patent: Nov. 3, 2015

(54) VASCULAR PLUG

(71) Applicant: COOK MEDICAL TECHNOLOGIES LLC, Bloomington, IN (US)

(72) Inventors: Tue Thuren Bodewadt, Solroed Strand (DK); Christina Rauff Hansen, Copenhagen (DK)

(73) Assignee: COOK MEDICAL TECHNOLOGIES llc, Bloomington, IN (US)

( * ) Notice: Subject to any disclaimer, the term of this patent is extended or adjusted under 35 U.S.C. 154(b) by 73 days.

(21) Appl. No.: 13/804,882

(22) Filed: Mar. 14, 2013

(65) Prior Publication Data
US 2014/0214073 A1    Jul. 31, 2014

(30) Foreign Application Priority Data

Jan. 25, 2013 (GB) .................................. 1301355.2

(51) Int. Cl.
*A61B 17/12* (2006.01)
(52) U.S. Cl.
CPC ..... *A61B 17/12109* (2013.01); *A61B 17/12159* (2013.01); *A61B 17/12181* (2013.01)
(58) Field of Classification Search
CPC ................... A61B 17/12109; A61B 17/12159; A61B 17/12022; A61B 17/12036; A61B 17/12093; A61F 2002/016
USPC .................................................. 606/213, 200
See application file for complete search history.

(56) References Cited

U.S. PATENT DOCUMENTS

| 5,645,558 | A | 7/1997 | Horton |
| 5,683,411 | A | 11/1997 | Kavteladze et al. |
| 6,063,113 | A | 5/2000 | Kavteladze et al. |
| 2004/0093015 | A1* | 5/2004 | Ogle ............................. 606/200 |
| 2006/0058833 | A1 | 3/2006 | VanCamp et al. |
| 2006/0106419 | A1* | 5/2006 | Gingras ........................ 606/213 |
| 2006/0206147 | A1* | 9/2006 | DeVore et al. ................ 606/213 |
| 2008/0262518 | A1 | 10/2008 | Freudenthal |
| 2009/0099647 | A1 | 4/2009 | Glimsdale et al. |
| 2009/0254172 | A1 | 10/2009 | Grewe |
| 2012/0283585 | A1* | 11/2012 | Werneth et al. .............. 600/508 |
| 2012/0330342 | A1* | 12/2012 | Jones et al. ................... 606/194 |

FOREIGN PATENT DOCUMENTS

WO    WO 2010/085344 A1    7/2010

* cited by examiner

*Primary Examiner* — Thomas McEvoy
*Assistant Examiner* — Julie A Szpira
(74) *Attorney, Agent, or Firm* — Brinks Gilson & Lione

(57) ABSTRACT

A vascular plug includes a plurality of cells which extend from a front face of the plug towards a distal end of the plug. The cells form at least a periphery of the plug and are in the preferred embodiment closed at their distal ends. The cells may form a central chamber to the plug or may extend across the entirety of the front face of the plug. The cells will fill with blood from the patient's vessel, to inflate the plug and create a barrier to fluid flow. Static blood within the plug will clot over time, creating enhanced occlusion. The plug can also be configured as a vascular filter.

19 Claims, 5 Drawing Sheets

VASCULAR PLUG

CROSS-REFERENCE TO RELATED APPLICATIONS

This application is related to and claims the benefit of priority to GB 1301355.2, filed on Jan. 25, 2013 which is incorporated herein by reference in its entirety.

TECHNICAL FIELD

The present invention relates to a vascular plug for occluding or providing filtration in a vessel. In the context of this patent application, the term vascular plug is used both for an occluding plug as well as for a filtration plug. An occluding plug may provide instantaneous occlusion, primarily by being impermeable to the passage of fluid, but may also provide occlusion by embolization, in which case the plug may be partially porous to allow reduced flow of fluid through the plug until sufficient thrombus formation has occurred at the plug to effect occlusion. A filtration plug will provide a porous mesh or frame through which blood may pass but which traps particulate material form the blood stream such as thrombi, plaque or other debris.

BACKGROUND ART

Vascular plugs have been known for a number of years. Many are in the form of a device which is implanted within a vessel of a patient and have a structure which closes off the vessel so as to occlude blood flow. Occluders of the plug type are preferable over more traditional forms of occlusion, such as vascular constrictors, which generally require an invasive medical procedure. Vascular plugs, on the other hand, can be deployed endoluminally in a significantly faster and less traumatic medical intervention.

Vascular plugs may be designed or used to provide temporary occlusion, for example to be effective only for the duration of a medical procedure or during a period of treatment. Occlusion may also be permanent, in which case the occluder will be left within the patient indefinitely.

There are two primary types of occluding vascular plug. The first promotes embolization within the vessel, for instance by slowing the flow of blood through the device, in some cases with the addition of embolization promoters. Such devices do not produce immediate occlusion of the vessel as they rely upon the formation of sufficient blood clotting to act as the occluding barrier. Thrombosis in sufficient amount to occlude can take hours, days or even weeks in some instances.

Another type of vascular plug has an impervious element, typically a membrane, which extends across the diameter of the vessel to create an instantaneous barrier to blood flow. In many cases such immediate occlusion is preferable. However, it is difficult to counter reliably the full force of the blood flow, leading to risk of migration of the device, loss of positional orientation, or failure to achieve a full seal against the vessel wall and thus in failure of the device. Furthermore, some such devices can fail to deploy properly in the vessel, leading them to being ineffective from the start.

Some examples of known vascular plugs can be found in U.S. Pat. No. 5,645,558, U.S. Pat. No. 5,683,411, U.S. Pat. No. 6,063,113, US-2008/262,518, US-2009/099,647 and WO-10/085,344.

DISCLOSURE OF THE INVENTION

The present invention seeks to provide an improved vascular plug. Some embodiments provide a plug of which at least a part is impervious so as to create substantially immediate occlusion of a vessel. In other embodiments, the vascular plug is permeable but designed to slow the flow of blood sufficiently so as to promote embolization. Other embodiments provide a plug with a filtration element such as a frame or mesh.

According to an aspect of the present invention, there is provided a vascular plug having a proximal face and a distal end; the plug including a plurality of cells, each cell including a body element formed by at least one wall and having a proximal end and a distal end, each cell including an opening at its proximal end; the proximal ends of said cells being at or adjacent the proximal face of the plug; said at least one wall of each cell at least partially extending across the cell opening.

This structure provides a plug formed with a plurality of cells which in practice will be filled with fluid from the blood stream, via the openings of the cells. The at least one cell wall which extends at least partially across the cell opening creates a barrier to fluid flow which in its minimal form will slow the flow of fluid, creating pressure within the cells to inflate these to a fully open configuration and thus form the open shape of the plug. Furthermore, the barrier to fluid flow will promote thrombosis and thereby the generation of an occlusion barrier within the cells.

The plug is preferably formed of a conformable material but may equally be made of a non-stretchable material. Examples of suitable materials include polyurethane, polyamide such as Nylon, polyether block amide such as Peebax, a thermoplastic elastomer (TPE), polytetrafluoroethylene (PFTE), silicone and the like. Thus, the plug can be radially contracted, for instance by folding and wrapping, for introduction into a patient endoluminally by means of an introducer assembly of known type. In some embodiments, the plug can be made of an elastic material, which enables the plug to expand by stretching at least in part until it is securely held against a vessel wall.

It is to be understood that the at least one wall of each cell extends at least partially across the cell opening in a position between the proximal face of the plug and the distal end thereof.

Advantageously, the cell openings form the proximal ends of the cells. In other words, the cells are substantially completely open at their distal ends.

In an embodiment, the cells include or are peripheral cells arranged in an annular ring extending around a proximal periphery of the plug. In practice, a part of the walls of the peripheral cells form the peripheral wall of the plug.

The plug may include a chamber disposed in the internal space between the peripheral cells, the chamber being open at the proximal face of the plug and being one of at least substantially closed or of a filter mesh at the distal end of the plug. The chamber is preferably formed by the walls of the cells, namely the internal sides of the walls of the cells.

Advantageously, the cells are adjacent one another and preferably share a common cell wall.

In another embodiment, there is included a plurality of chambers within the internal space between the peripheral cells, the chambers being open at the proximal face of the plug and being at least substantially closed at the distal end of the plug. The chambers are preferably formed at least in part by the internal sides of the walls of the peripheral cells. The internal chambers are advantageously formed by common chamber walls, and the internal peripheral cell walls. In the preferred embodiment, the chambers and peripheral cells have shapes which tessellate at the proximal face of the plug.

The walls of the internal chambers are advantageously made from the same material as the peripheral cells.

The cells may include end walls at their distal ends, which end walls at least partially close off the distal ends. Most preferably, the end walls completely close off the distal ends of the cells, thereby to cause the cells to have the form of blind bores. In another embodiment, the cell walls define a labyrinthine path therethrough. In yet another embodiment, the cell walls include a constriction in the internal volume of the cells.

In an embodiment, the plug has a tapering shape, as do at least some of the cells or chambers of the plug. Preferably, the peripheral cells taper towards the distal end of the plug.

The plug may be impermeable or partially permeable. An impermeable plug can provide substantially instantaneous occlusion of a body vessel upon its deployment, whereas a partially permeable plug will occlude the vessel after the creation of thrombi in the vessel, promoted by the slowing of the flow of blood and creation of zones of static blood flow. A permeable plug can provide for filtration of debris and thrombi from the blood stream.

An impermeable occluder can be formed by the use of impermeable materials for the walls of the cells and other walls of the plug. A partially permeable occluder can be formed by creation of one or more apertures in the walls of the plug and/or by the use of permeable material.

Other features and advantages of the teachings herein will become apparent from the specific description and the accompanying drawings.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There are described below various embodiments of vascular plug designed to be implanted endoluminally into a patient so as to close off the flow of or filter blood within the vessel in which the plug is deployed. The plug can be made substantially impervious, so as to effect occlusion substantially immediately upon deployment of the device. In other embodiments the plug may be permeable but of a structure which substantially reduces the flow of fluid therethrough, so as to cause occlusion primarily by promoting thrombosis within the vessel, as the result of the creation of zones of static blood flow.

As will become apparent from the teachings herein, the various embodiments of plug described below provide a plurality of cells within the structure of the plug which fill with fluid so as to cause the plug to acquire an inflated or filled volume which radially expands the plug into abutment with the internal vessel walls. This expansion holds the plug in place and closes off the vessel. The various cells of the plug preferably have proximal open ends which are coplanar with the front face of the plug.

Figure 1:
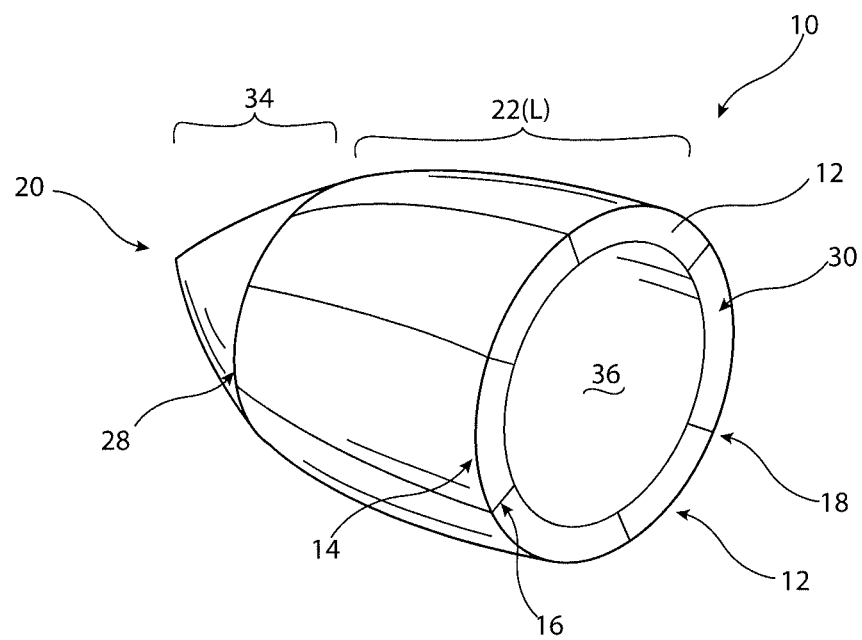
FIG. 1 is a perspective view of a first embodiment of vascular plug.

FIGS. 1-4 show a first embodiment of plug 10 which is formed of a plurality of peripheral cells 12 which extend around the circumferential periphery 14 of the plug 10. The cells 12 adjoin one another at common walls 16 and extend from a proximal face 18 of the plug 10 towards the plug's distal end 20. In the view of FIG. 1, the cells 12 provide a body portion 22 to the plug 10, which the distal end 20 of the plug tapers to a point.

Figure 2:
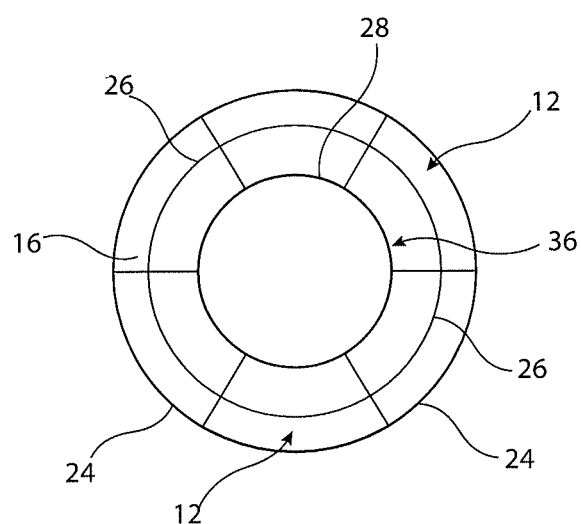
FIG. 2 is a front elevational view of the plug of FIG. 1.

With reference also to FIG. 2 each cell 12 is formed of an outer wall 24, which forms the outer peripheral wall of the plug 10, and an inner wall 26 which forms the inner wall of the plug 10. The embodiment of FIGS. 1 to 4 has the cells 12 which bulge from the proximal face 18 and then taper generally in the distal direction of the plug 10 so as to have distal ends 28 which have a smaller diameter than the diameter of the plug 10 at its front face 18.

In the preferred embodiment, the walls 16, 24 and 26 of the cells 12 are all made of the same material and a material which is impermeable. Examples of suitable materials include polyurethane, polyamide such as Nylon, polyether block amide such as Peebax, a thermoplastic elastomer (TPE), polytetrafluoroethylene (PFTE), silicone and the like.

The proximal ends 30 of the cells 12 are in the preferred embodiment entirely open, that is they have no wall or other barrier between the walls 16, 24, 26. The distal ends 28 of the cells 12 are in the preferred embodiment closed, by walls made of the same material as the side walls 16, 24, 26. In other embodiments, though, the distal end 28 of the cells 12 may be partially closed, for instance by a wall which extends only part-way across the area of the distal ends, by a wall which has apertures or openings therein, by a wall made of porous material or the like. In some embodiments, the distal end 28 of the cells 12 may be open.

In the embodiments shown in FIGS. 1 to 4, beyond the distal end 28 of the cells 12, the plug 10 is provided with an end piece 34 which tapers to the distal end 20 of the plug 10. The end piece 34 is preferably made of an impermeable or substantially impermeable material, typically the same material as that used to form the walls 16, 24, 26 of the cells 12 in the case where the plug 10 is constructed as an occluder. In the case where the plug 10 is configured as a filter, the end piece 34 may be a mesh of mesh size sufficient to trap debris in the mesh but open enough to allow relatively free passage of blood therethrough. The end piece 34 is preferably integral with at least the outer walls 24 of the cells, in order to give the plug a uniform outer surface. The end piece 34 may be made on a single layer of material, rather than a double layer as are the cells 12, which enhances the wrappability of the plug 10 for delivery purposes.

As will be apparent particularly from FIG. 1, the peripheral cells 12 form an internal chamber 36 to the plug 10 which could be described as the principal chamber of the device 10.

Figure 3:
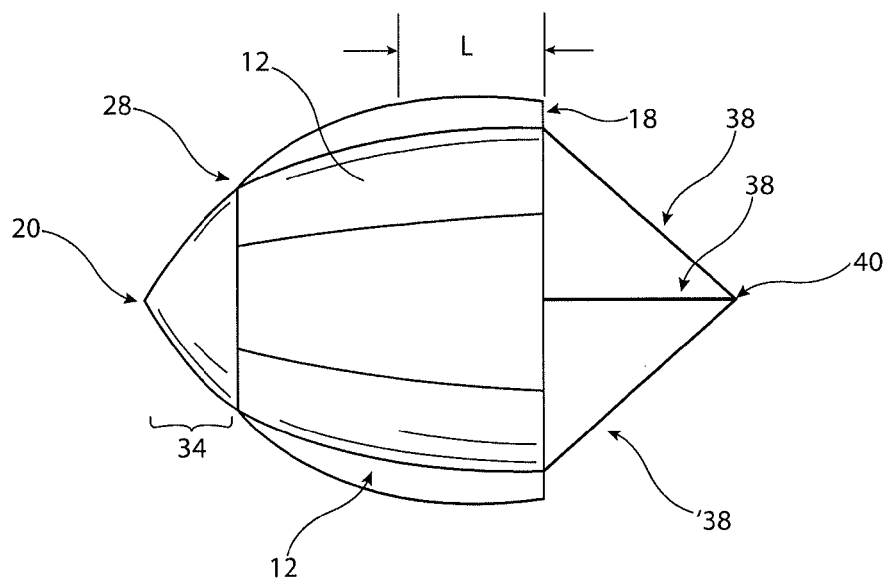
FIG. 3 is a side elevational view of the plug of FIG. 1.

FIG. 3 shows the inclusion of a plurality of tethers 38 which extend from the proximal ends of the cells 12 and proximal face 18 of the plug 10 towards a central point 40 and may include a connection element such as a hook, ring or the like useful for manoeuvring the plug 10 during the deployment procedure and, as appropriate, a subsequent retrieval procedure if it is desired to do so after the end of a deemed period of treatment. The tethers 38 may usefully be threads of polyamide (such as Nylon) or a suture thread. They are suitably tied or bonded to the proximal end of the plug 10.

Figure 4:
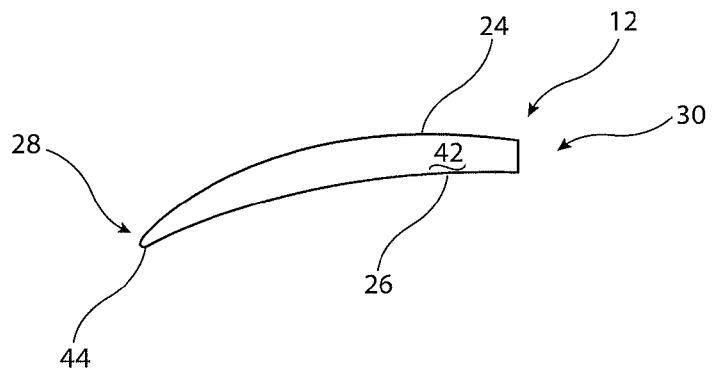
FIG. 4 is a longitudinal cross-sectional view of a cell of the plug of FIG. 1.

Referring now to FIG. 4, there is shown a cross-sectional view of an embodiment for one of the cells 12 of the plug 10 of FIG. 3. In this embodiment, the outer and inner walls, 24, 26 of each cell 12 taper towards one another from the proximal end 30 towards the distal end 28 of the cell 12 and define therewithin a chamber 42 which has a narrowing cross-sectional area in the direction towards the distal end 28 of the cells. In this example, the outer and inner walls 26 converge to a point 44 at which they are connected to one another, at the distal end 28 of the cells. In other embodiments there could be provided a separate end wall extending across a space between the outer and inner walls 24, 26.

Thus, in the embodiment of FIG. 4, the cells 12 are entirely closed at their distal end. However, as explained above, they may be partially open, for instance by having one more apertures in completely closed distal end 28, while in yet other embodiments the end 28 may be completely open, in dependence upon the design of the cells 12, explained in further detail below.

Given their open end 30, the cells 12 will in use become filled with blood from the patient's vessel. The force of the blood flow, that is the pressure of blood within the cells 12, will cause these to expand to their maximum dimensions, determined by the walls 16, 24, 26 of the cells and thus, particularly with filling of the central chamber 36 of this embodiment, will cause the plug 10 to adopt the fully open or inflated shape shown in FIGS. 1 to 4. In the case where the cells 12 are closed, the blood would then become static within the plug 10.

It is not necessary for the cells to be fully closed in order for them to be inflated by the pressure of blood flow within the patient's vessel. As long as the cells 12 have a flow reducing character, this will cause a build-up of pressure within the cells and thus within the plug in order to cause them to fill. Such a characteristic can be achieved by provision of a wall which at least partially closes off the area of the opening of the proximal end 30 of the cells 12. That wall could, for instance, be an end wall (full or partial) at the distal end 28 of cell 12, a curved outer wall 28 (or inner wall 26), convergence of the outer and inner walls 24, 26 or any other of the walls forming the cells 12. These will cause a barrier to unimpeded blood flow and thus a build-up of fluid pressure. This is not only useful in inflating the plug 10 but also in slowing/stopping the flow of fluid to create occlusion (instantaneously or by generation of thrombosis).

The arrangement of the cells 12, which are at the periphery of the plug 10, creates in practice a wall structure at the outside periphery of the plug 10 which will have a certain strength and resistance to pressure imposed on the device 10. This strength is produced by the build-up of fluid pressure within the cells 12, which will enable the plug 10 to apply an opening and therefore holding pressure against the vessel walls in order to seal the plug around the vessel walls and also in order to hold the plug 10 in place within the vessel to prevent or minimise the risk of its migration.

In some embodiments, the outer surface of the outer walls 24 of the cells 12 and thus of the plug 10, may be roughened or textured so as to increase the frictional resistance of the plug when in abutment against the vessel wall. This enhances its resistance to migration and thus improves the positional stability of the plug 10 in a patient's vessel. In other embodiments, the outer surface 24 could be provided with barbs or other anchoring elements, designs for which will be apparent to a person skilled in the art.

The plug 10 is most preferably formed of materials (some examples being given above) which are conformable and thus able to be radially constrained, typically by wrapping and folding, so that the entire structure of the plug 10 can be minimised in terms of its radius, to enable the plug 10 to be delivered to the site of treatment endoluminally by means of an introducer assembly of the type known in the art. Once delivered in a wrapped configuration, the plug would unwrap and fill out, in large part by the blood flow within the vessel in which the plug is deployed. In this regard, the provision of the tethers 38 and connecting element 40 can be used to hold the plug 10 in position while this expands and fills with fluid, that it until the plug has secured itself to the vessel walls. This would be achieved by a suitable restraining element of the introducer assembly, which can hook onto the connecting element 40 during the implantation procedure.

Once the plug 10 has been deployed in a patient's vessel, blood will stagnate within the peripheral cells of the plug 10. This will secure the plug 10 in place.

With reference again to FIG. 3, as well as FIG. 1, it will be appreciated that the outer wall 24 of the plug 10 has a given length, L, which is cylindrical or generally cylindrical, and which provides a contact surface area of the plug 10 which will come into abutment of the vessel wall, useful in ensuring good contact and holding of the plug within the vessel.

Figure 5:
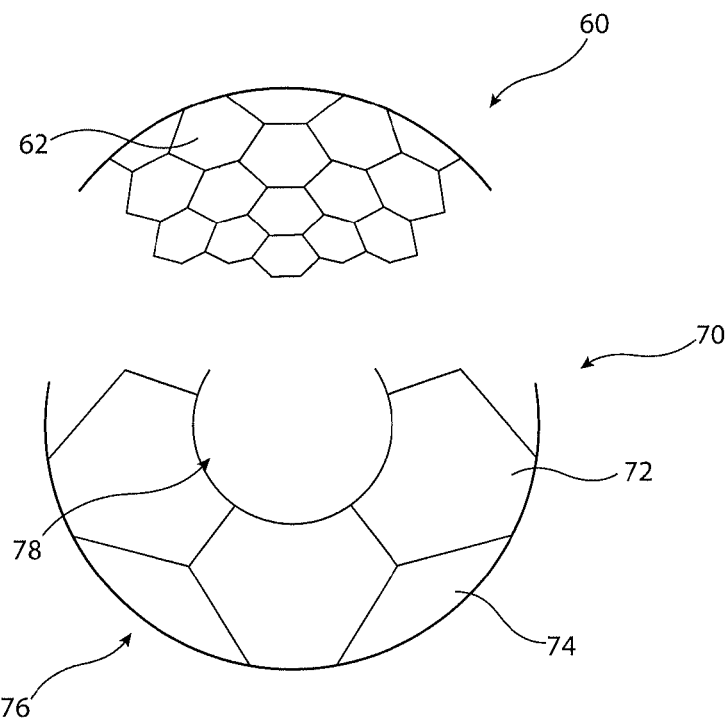
FIG. 5 shows front elevational views of two different embodiments of plug structure according to the teachings herein.

Referring now to FIG. 5, there are shown two other examples of plug 60, 70 having characteristics in common with the embodiments of FIGS. 1 to 4. The views of FIG. 5 are front elevational views, thus showing the front face of the plug. Referring first to the embodiment of plug 60, this is formed of a plurality of cells 62 which extend from the front face of the plug 60 towards its distal end (that is into the paper in the view of FIG. 6) and these have side walls having characteristics similar to the cells 12 of the embodiments of FIGS. 1 to 4. The cells 62 have different sizes and shapes, so as to tessellate across the front face of the plug 60 and form the entirety of the front face of the plug 60, in other words, without there being a central chamber 36 as in the embodiments of FIGS. 1 to 4. The cells 62 provide the same function as the cells 12 of the embodiments of FIGS. 1 to 4.

The embodiment of plug 70 includes a plurality of large cells 72 of generally polygonal shape, with interleaved edge cells 74 which, together with the outer walls of the cells 72 form a smooth outer periphery 76 of the plug 70. This embodiment also provides a main central chamber 78 to the plug 70, similar to the chamber 36 of the embodiment of FIGS. 1 to 4, but which will generally have a smaller volume as the result of the greater volume of the cells 72, 74. Again, the cells 72, 74 will extend towards the distal end of the plug and thus into the paper in the view of FIG. 5.

Figure 6:
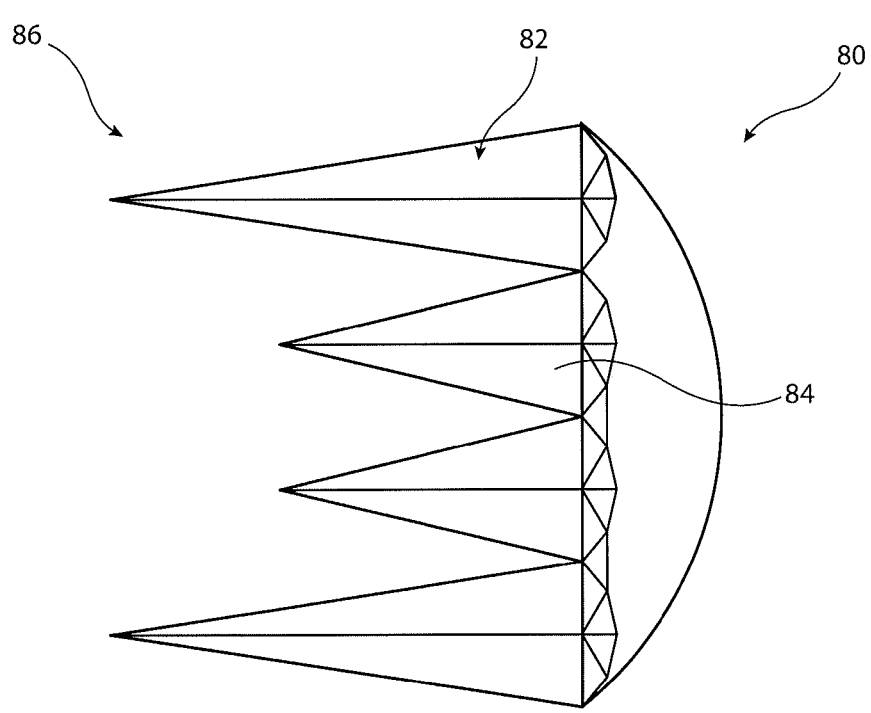
FIG. 6 is a side elevational view of another embodiment of plug.
Figure 7:
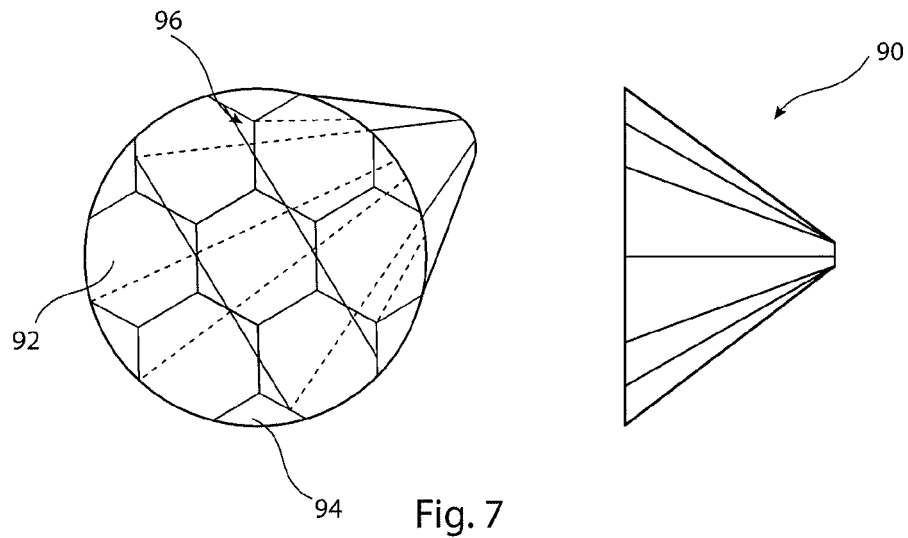
FIG. 7 shows front and side elevational views of yet another embodiment of plug.

FIG. 6 shows in schematic form another embodiment of plug 80 having characteristics which could be incorporated in the other embodiments disclosed herein, that is including a plurality of cells 82 and 84 which tessilate across the front face of the plug and which have tapering walls which end at tips towards the distal end 86 of the plug 80. The cells 82, 84 can be interleaved with one another across the frontal area of the plug 80, but in other embodiments they still provide a central chamber as per the chambers 36 and 78 of the embodiments of FIGS. 1 to 5. Where the cells 82, 84 cover the complete front surface of the plug 80, they may not taper towards a single distal point of the plug 80 but may on the other hand be radially spread from one another as depicted in FIG. 7, which would increase the length of contact of the plug 80 against the vessel wall, typically up to the entire length of the larger and longer cells 82. This can provide improved positional and orientational stability of the plug within the vessel and improved resistance to migration.

FIG. 7 shows another embodiment of plug 90, having a generally conical shape and formed of a plurality of hexagonal cells 92 which extend across the front face of the plug 90. Interleaving cells 94 create a generally uniform opening diameter to the plug 90. In the spaces between adjacent cells 92 where provided baffles or walls 96 to close off any gaps between the cells 92, thereby to ensure that fluid flows solely into the cells 92 of the plug.

Figure 8:
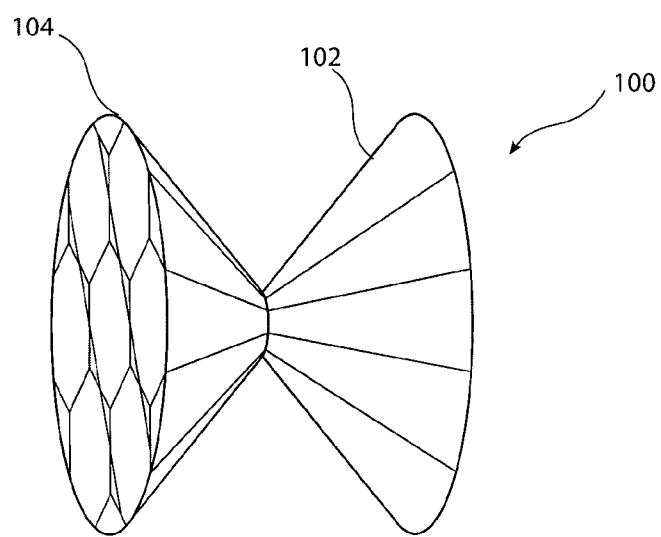
FIG. 8 is a perspective view of an embodiment of double ended plug according to the teachings herein.

Referring now to FIG. 8, there is shown another embodiment of plug 100 similar to the embodiment of plug 90 and which is provided with oppositely disposed conical portions 102, 104, to create a double ended device suitable for implantation into vessels which are liable to fluid backflow and/or in any orientation in a vessel. The plug 100 has the features and characteristics described above with respect to the other embodiments. It is to be understood that all of the embodiments disclosed herein could be arranged as double ended devices in similar fashion to FIG. 8.

Figure 9A:
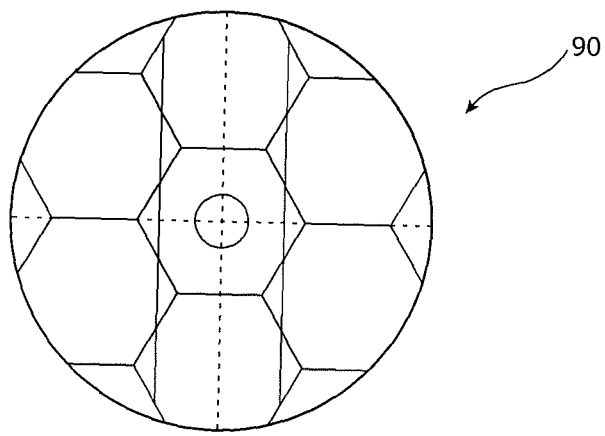
FIG. 9 shows various views of the plug of FIG. 9 in the process of radial contraction by wrapping and folding for delivery.
Figure 9B:
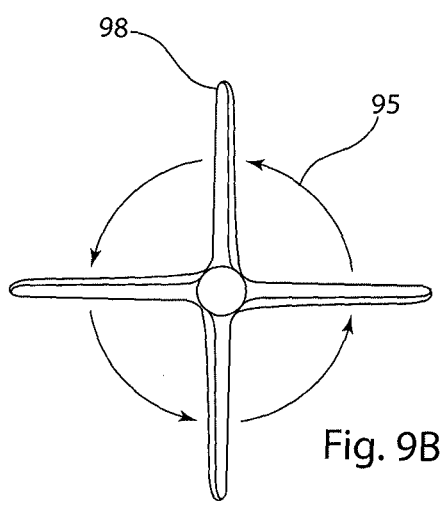
Figure 9C:
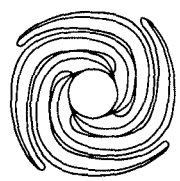

With reference now to FIG. 9, this shows the stages of wrapping and folding the plug 90 of FIG. 8 for delivery purposes. The plug 90, from its open configuration shown in FIG. 9A is wrapped as shown in FIG. 9B to create four wings 98 of compressed plug material, which is then folded as shown in FIG. 9C, in the direction of the arrows 95 in FIG. 9B, so as to radially compress the plug 90 so that it may be then delivered through the sheath of an introducer assembly, in known manner.

It will be appreciated that the embodiments of FIGS. 5, 7 and 8 are most suitable as occluders, although they may be configured as filters by constructing some of the cell walls with open mesh material.

The material of the walls forming the plugs taught herein may be substantially inelastic but in other embodiments may be elastic, to enable the plug to expand by stretching until it fills the space within a vessel, that is comes to abut the vessel walls.

It is preferred that the walls of the plug are of a single layer of material, which enhances flexibility and wrappability of the plug. It is not excluded, however, that the walls may be of a plurality of layers. Furthermore, in some embodiments, there may be provided strengthening elements within at least a part of the plug walls, for example, elements extending in the longitudinal direction of the plug (from the front face to the distal end), on or within the outer walls of the plug. A variety of different arrangements will be apparent to a person skilled in the art on the basis of common general knowledge and the teachings herein.

All of the embodiments of vascular plug disclosed herein and covered by the claims could be configured to be deliverable over a guide wire, in which case the plug will have an aperture or hole at its distal end able to accommodate the passage of a guide wire. The aperture or hole in most cases can be sufficiently small to be able to be closed by embolization of blood at the hole or aperture. In some embodiments there may be provided thrombolytic elements such as fibres or an agent, while in other embodiments there may be provided a valve. Of course, in the case of a plug configured as a filter, the hole for the passage of a guide wire may be sufficiently small that it can be left open.

Other modifications and combinations will be apparent to the person skilled in the art having regard to teachings herein and those modifications are to be considered as a part of the disclosure herein.

The invention claimed is:

1. A vascular plug having a proximal face and a distal end; the plug including a plurality of peripheral cells, each peripheral cell including a body element formed by at least one wall, wherein the wall is between adjacent cells, and each peripheral cell having a proximal end and tapering to a distal end such that each body element has a cross-sectional area which is narrower at the distal end than at the proximal end, each peripheral cell including an opening at its proximal end; the proximal ends of said peripheral cells being at or adjacent the proximal face of the plug such that the peripheral cells have shapes which tessellate around a periphery of the proximal face of the plug in an annular arrangement.

2. A vascular plug according to claim 1, wherein the plug is formed of a conformable material.

3. A vascular plug according to claim 1, wherein the plug is formed of an elastic material.

4. A vascular plug according to any preceding claim, wherein the cell openings form the proximal ends of the cells.

5. A vascular plug according to claim 1, wherein a part of the walls of the peripheral cells form the peripheral wall of the plug.

6. A vascular plug according to claim 1, wherein the plug includes a chamber disposed in an internal space between the peripheral cells, the chamber being open at the proximal face of the plug and being, at the distal end of the plug, one of at least substantially closed and of filter material.

7. A vascular plug according to claim 6, wherein the chamber is formed by the walls of the cells.

8. A vascular plug according to claim 1, wherein cells are adjacent one another and share a common cell wall.

9. A vascular plug according to claim 1, wherein there is included a plurality of chambers within the internal space between the peripheral cells, the chambers being open at the proximal face of the plug and being at least substantially closed at the distal end of the plug.

10. A vascular plug according to claim 9, wherein the chambers are formed at least in part by the internal sides of the walls of the peripheral cells.

11. A vascular plug according to claim 9, wherein the internal chambers are formed by common chamber walls, and the internal peripheral cell walls.

12. A vascular plug according to claim 9, wherein the chambers have shapes which tessellate at the proximal face of the plug.

13. A vascular plug according to claim 9, wherein the walls of the internal chambers are made from the same material as the peripheral cells.

14. A vascular plug according to claim 1, wherein the cells include end walls at their distal ends, which end walls at least partially close off the distal ends.

15. A vascular plug according to claim 14, wherein the end walls completely close off the distal ends of the cells, thereby to cause the cells to have the form of blind bores.

16. A vascular plug according to claim 1, wherein the cell walls define a labyrinthine path through the plug.

17. A vascular plug according to claim 1, wherein the cell walls include a constriction in the internal volume of the cells.

18. A vascular plug according to claim 1, wherein the plug has a tapering shape.

19. A vascular plug according to claim 1, wherein the plug is one of impermeable and partially permeable.

\* \* \* \* \*